(12) United States Patent
Heine et al.

(10) Patent No.: US 10,007,982 B2
(45) Date of Patent: Jun. 26, 2018

(54) AUTOMATED PERCENTAGE OF BREAST DENSITY MEASUREMENTS FOR FULL FIELD DIGITAL MAMMOGRAPHY

(71) Applicants: H. LEE MOFFITT CANCER CENTER AND RESEARCH INSTITUTE, INC., Tampa, FL (US); MAYO FOUNDATION FOR MEDICAL EDUCATION AND RESEARCH, Rochester, MN (US)

(72) Inventors: John J. Heine, New Port Richey, FL (US); Thomas A. Sellers, Tampa, FL (US); Celine M. Vachon, Rochester, MN (US); Erin E. Fowler, Tampa, FL (US)

(73) Assignees: H. Lee Moffitt Cancer Center and Research Institute, Inc., Tampa, FL (US); Mayo Foundation for Medical Education and Research, Rochester, MN (US)

( * ) Notice: Subject to any disclaimer, the term of this patent is extended or adjusted under 35 U.S.C. 154(b) by 177 days.

(21) Appl. No.: 14/893,603

(22) PCT Filed: May 30, 2014

(86) PCT No.: PCT/US2014/040140
§ 371 (c)(1),
(2) Date: Nov. 24, 2015

(87) PCT Pub. No.: WO2014/194160
PCT Pub. Date: Dec. 4, 2014

(65) Prior Publication Data
US 2016/0110863 A1    Apr. 21, 2016

Related U.S. Application Data

(60) Provisional application No. 61/828,780, filed on May 30, 2013, provisional application No. 61/828,971, filed on May 30, 2013.

(51) Int. Cl.
*G06K 9/00*    (2006.01)
*G06T 7/00*    (2017.01)
(Continued)

(52) U.S. Cl.
CPC .......... *G06T 7/0012* (2013.01); *A61B 6/502* (2013.01); *G06K 9/0051* (2013.01); *G06K 9/527* (2013.01);
(Continued)

(58) Field of Classification Search
CPC ....... G06T 7/44; G06T 7/0012; G06K 9/0051; G06K 9/527; G06K 9/623
(Continued)

(56) References Cited

U.S. PATENT DOCUMENTS

2009/0041373 A1 *  2/2009  Incesu ................ G06T 5/002
                                                           382/264
2009/0232376 A1    9/2009  Raundahl et al.
(Continued)

FOREIGN PATENT DOCUMENTS

WO       2012/082994       6/2012
WO    WO 2012082994 A2 *  6/2012  ........... A61B 5/4312

OTHER PUBLICATIONS

Heine, J.J., et al., "Spectral analysis of full field digital mammography data," Medical Physics, vol. 29, No. 5, 2002, pp. 647-661.
(Continued)

*Primary Examiner* — Van D Huynh
(74) *Attorney, Agent, or Firm* — Meunier Carlin & Curfman LLC

(57) ABSTRACT

An automated percentage of breast density measure (PDa) that analyzes signal dependent noise (SDN) based on a wavelet expansion using full field digital mammography (FFDM). A matched case-control dataset is used with images acquired from a specific direct x-ray capture FFDM
(Continued)

system. PDa is applied to the raw and clinical display representation images. Transforming (pixel mapping) of the raw image to another representation (raw-transformed) is performed using differential evolution optimization and investigated the influence of lowering the native spatial resolution of the image by a one-half. When controlling for body mass index, the quartile specific ORs for the associations of PDa with breast cancer varied with representation and resolution. PDa is a valid automated breast density measurement for a specific FFDM technology and compares well against PD (operator-assisted or the standard) when applied to either the raw-transformed or clinical display images from this FFDM technology.

10 Claims, 3 Drawing Sheets

(51) Int. Cl.
| | |
|---|---|
| *G06K 9/52* | (2006.01) |
| *A61B 6/00* | (2006.01) |
| *G06K 9/62* | (2006.01) |
| *G06T 7/41* | (2017.01) |

(52) U.S. Cl.
CPC .............. *G06K 9/623* (2013.01); *G06T 7/41* (2017.01); *G06K 2209/05* (2013.01); *G06T 2207/10116* (2013.01); *G06T 2207/20076* (2013.01); *G06T 2207/30068* (2013.01)

(58) Field of Classification Search
USPC ........................................................ 382/132
See application file for complete search history.

(56) References Cited

U.S. PATENT DOCUMENTS

| | | |
|---|---|---|
| 2009/0324049 A1 | 12/2009 | Kontos et al. |
| 2010/0124364 A1 | 5/2010 | Huo et al. |
| 2011/0013819 A1* | 1/2011 | Raundahl ............... G06K 9/527 |
| | | 382/132 |
| 2014/0219552 A1* | 8/2014 | Porikli ................... G06T 5/002 |
| | | 382/155 |

OTHER PUBLICATIONS

International Search Report and Written Opinion, dated Oct. 10, 2014, received in connection with International Patent Application No. PCT/US2014/040140.

International Preliminary Report on Patentability and Written Opinion, dated Dec. 1, 2015, received in connection with International Patent Application No. PCT/US2014/040140.

* cited by examiner

AUTOMATED PERCENTAGE OF BREAST DENSITY MEASUREMENTS FOR FULL FIELD DIGITAL MAMMOGRAPHY

STATEMENT REGARDING FEDERALLY SPONSORED RESEARCH OR DEVELOPMENT

This invention was made with Government Support under Grant No. CA114491 awarded by the National Institutes of Health. The Government has certain rights in the invention.

FIELD OF THE DISCLOSURE

The present disclosure relates to a mammography; more specifically to methods of analyzing mammography results for estimating breast cancer risk for related applications such as for the detection of breast cancer.

BACKGROUND

Breast density is a significant breast cancer risk factor assessed from mammograms. Due to measurement difficulties and the lack of automation, breast density is used mainly for research purposes and not for breast cancer risk purposes in the clinical environment.

Full field digital mammography (FFDM) is replacing film-mammography. This may be a benefit for automated measurement developments because film-images are sometimes difficult to process in part to markings and anomalous regions located in non-breast area portion of the image. In contrast, FFDM images lack off-breast area anomalies. Although there are various FFDM manufactures, there are two predominant FFDM technologies used today consisting of direct and indirect x-ray capture systems, producing images with different characteristics. The data representation produced by FFDM systems may vary due to the x-ray detection technology, x-ray generation, or post acquisition processing. FFDM systems produce both raw and processed representation mammograms.

Typically, the processed images are used for clinical display purposes, whereas the raw images are normally not considered in the clinical evaluation. A given clinical display, or processed image, is derived from its respective raw image with methods developed by the unit's manufacturer and may be mated to its clinical display apparatus. It is not clear if both representations support breast density measurements similarly, if there is a preferred representation, or what role the technology plays relative to automated measurements. It is often the case that operator-assisted methods can overcome data representation differences that appear as obstacles for automated measurements. Therefore, when developing an automated breast density measurement, it is important to understand factors that may influence its performance, which could either attenuate or enhance its associations with breast cancer.

SUMMARY

The present disclosure is directed to measurement of breast density (PD). The present disclosure is also directed to an analogous automated measure for FFDM applications built upon an automated breast density measurement ($PD_a$) that provides the same metric as PD. The measurement is an evolution of modeling the Fourier spectral density of digitized film mammograms as an inverse power-law. The power-law behavior for a given mammogram is estimated, and its shape removed with a deconvolution process, resulting in a noise-field (i.e. the deconvolved image). Due to the inverse power-law, the deconvolution process in this specific application equates with a high-pass filtering operation, producing the filtered-image. Areas of higher spatial variation may be noted (the marker of the tissue type) in the filtered-image corresponded with areas of increased mammographic density in the digitized mammogram (i.e. the tissue), which is the signature of signal dependent noise (SDN). A statistical method may be developed for detecting these areas of increased variation in the filtered-image, forming the basis of the $PD_a$ technique. In some implementations, the deconvolution process may be replaced (approximated) with a high-pass wavelet filter, increasing the algorithm speed, and the $PD_a$ measure was validated using digitized film-mammograms and breast cancer status as the endpoint.

In some implementations, an evaluation of $PD_a$ processing is performed to describe the data representation conditions for its effective operation. The $PD_a$ may be applied to a case-control dataset for patients with images acquired from a specific direct x-ray capture FFDM technology and used mammograms in both raw and processed image representations. An empirically determined data transform may be performed as a preprocessing step for the raw images to improve the $PD_a$ processing, giving a third format, defined as the raw-transformed representation for the reasons discussed below. An evolutionary optimization strategy may be used to determine the parameters of this transform.

In some implementations, the impact on the $PD_a$ performance is investigated when reducing the native image spatial resolution by a factor of one-half. The $PD_a$ may be applied to the various representations and compared the respective associations with breast cancer. These associations may be compared with those provided by PD (from the Cumulus program), considered as the baseline comparison.

Moreover, it is not expected to find heterogeneity in the respective $PD_a$ findings across the data representations processed in this report. Therefore, the differences relevant to the $PD_a$ processing may be characterized by generalizing SDN analysis methods developed previously, noting that $PD_a$ operates by applying a statistical test to this noise. The SDN analysis also may rely upon wavelet processing.

Additional features and advantages of the invention will be made apparent from the following detailed description of illustrative embodiments that proceeds with reference to the accompanying drawings. For example, in accordance with other aspects of the invention, the risk measure may include any combination of order measures discussed above.

BRIEF DESCRIPTION OF THE DRAWINGS

For a fuller understanding of the invention, reference should be made to the following detailed description, taken in connection with the accompanying drawings, in which.

DETAILED DESCRIPTION

Figure 1:
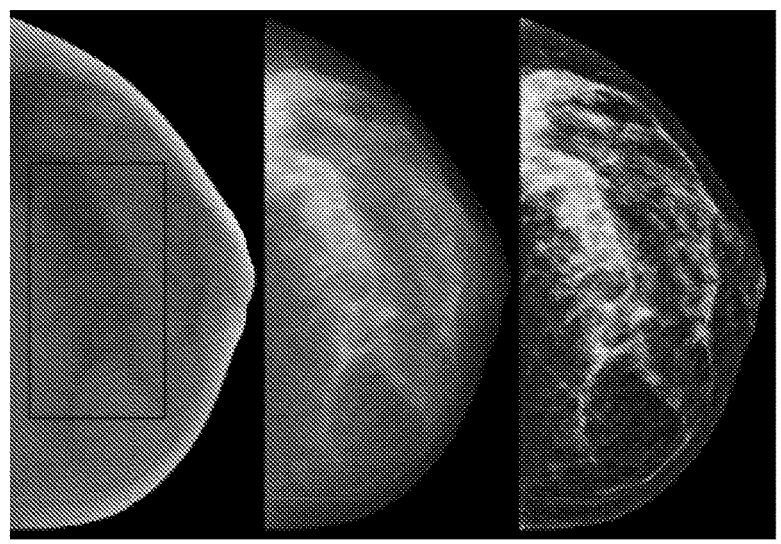
FIG. 1 illustrates a breast density measurement receiver operating curve analysis.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Breast density is a significant breast cancer risk factor that can be evaluated from mammograms. A reproducible automated measurement is required for full field digital mammography (FFDM) to support of large-scale breast cancer risk applications in the clinical setting. In furtherance of the above, an automated percentage of breast density measure ($PD_a$) is evaluated that analyzes signal dependent noise (SDN) based on a wavelet expansion. The influence of the FFDM image pixel representation is assessed and spatial resolution on this measure's association with breast cancer to understand factors that may influence its performance. A matched case-control dataset (200-400) may be used with images acquired from a specific direct x-ray capture FFDM system. As will be described, $PD_a$ may be applied to the raw and clinical display representation images. Transforming of the (pixel mapping) the raw image to another representation (raw-transformed) may be performed for improving the $PD_a$ performance using differential evolution optimization and investigated the influence of lowering the native spatial resolution of the image by a one-half. SDN characterization and non-linear regression modeling were used to understand the conditions that influence the $PD_a$ performance. An operator-assisted percentage of breast density measure (PD) may be applied to the raw images as a standard for measurement comparison. Conditional logistic regression was used to estimate the odd ratios (ORs) with 95% confidence intervals for all measurements.

When controlling for body mass index (BMI), the quartile specific ORs for the associations of $PD_a$ with breast cancer varied with representation and resolution: (a) [OR: 1.0 (ref.), 1.27 (0.74, 2.19), 1.86 (1.05, 3.28), 3.00 (1.67, 5.38)] for the raw-transformed images; (b) [OR: 1.0 (ref.), 1.79 (1.04, 3.11), 1.61 (0.90, 2.88), 2.94 (1.66, 5.19)] for the clinical display images; and (c) [OR: 1.0 (ref.), 0.93 (0.53, 1.64), 1.27 (0.74, 2.21), 2.21 (1.26, 3.87)] for the half-resolution raw-transformed images. In contrast, $PD_a$ produced little when applied to the raw images (findings not shown). When controlling for BMI, the associations provided by PD, [OR: 1.0 (ref.), 1.59 (0.93, 2.70), 1.70 (0.95, 3.04), 2.04 (1.13, 3.67)], were within the ranges of the various $PD_a$ findings. The SDN analysis showed that a positive concavity relationship between the signal (adipose or dense tissue) and the noise (the maker of adipose of dense tissue) is required for the $PD_a$ processing. Positive concavity was exhibited more strongly for the raw-transformed representation than the clinical display or raw image representations. Lowering the image resolution decreased the $PD_a$ performance by diminishing the required concavity characteristic.

Thus, as will be described below, a SDN technique will be presented that quantifies the conditions for the effective $PD_a$ operation. As such, the $PD_a$ is a valid automated breast density measurement for a specific FFDM technology and compares well against PD (the standard) when applied to either raw-transformed or clinical display images from this FFDM technology.

Methods

Study Population and Mammography

The patients for this study were derived from the Mayo Mammography Health Study (MMHS) cohort, Rochester Minn. Briefly, the MMHS is an ongoing cohort study of women living in Minnesota, Wisconsin, or Iowa who are older than 35 years, had screening mammography at the Mayo Clinic between 2003 and 2006, and have no personal history of breast cancer. Participants completed a questionnaire and provided written informed consent to use their mammograms, medical records, and blood samples and to link their data to state cancer registries. The 19,924 subjects who participated (51% of the 38,883 subjects who were eligible) were followed up for incident cancer events through the tri-state cancer and Mayo Clinic tumor registries. Through Dec. 31, 2008, a total of 290 incident and histologically confirmed primary breast cancers were identified. To date, the study has 200 breast cancer cases and 400 matched controls (2 per case) with mammograms available from a specific type of FFDM technology. The controls were age matched to the cases. These patients were used to form the case-control dataset for this study.

All patient mammograms were acquired from Hologic Selnia FFDM units. This FFDM unit has 70 micron spatial resolution (pixel pitch). The detector has a 24 cm×29 cm field of view. The raw and processed representation images have 14-bit and 12-bit per pixel dynamic range, respectively. Screening mammograms are often acquired with two images sizes depending on compression paddle choice: 2560×3328 pixels or 3328×4098 pixels. The cranial caudal (CC) views were used as the study images only. For cases, the non-cancerous breast was used. For controls, the breast-side was selected randomly (CELINE is this correct).

Statistical Analysis

Patient characteristics and breast measures were summarized with the distribution mean and standard deviation (SD). For each breast density measure, quartiles were defined based on the distribution of that density measure among the control subjects. Controls (n=400) were matched to cases (n=200) on age. Conditional logistic regression was used in the primary analysis to model and compare the association between quartile measures of PD, and breast cancer status, with the lowest quartile serving as the reference. Continuous measures of breast density (PD and the $PD_a$ variants) were also investigated. As the primary metric, the magnitudes of the associations were summarized by odds ratios (ORs) with 95% confidence intervals (CIs). For continuous breast density variables, the ORs presented as per distribution standard deviation increase, calculated from the control distribution. The breast density models are simultaneously adjusted for body mass index (BMI) measured in kg/m². Additionally, as a secondary means of comparison, the area under the receiver operating characteristic curve (Az) was computed as a summary of the ability of each model to discriminate between cases and controls. To match the study design, Az was calculated only within matched case-control pairs. A 95% confidence interval was calculated for each Az based on 1000 bootstrap samples and these samples were also used to compare Az. Pearson correlation coefficients were calculated to measure association between continuous breast density measurements.

Operator Assisted Percentage of Density

The PD association with breast cancer may be used as a standard reference point for the $PD_a$ findings. Because the focus is the $PD_a$ application, the Cumulus analysis may be restricted to the raw images only. PD was estimated from the raw representation FFDM images in DICOM format with the Cumulus3 software (University of Toronto). The dataset consisting of all cases and matched control images were de-identified and randomized. The reader (JH) was blinded to the case-control status and original image identifiers. When using Cumulus, the operator sets window adjustments and thresholds for each image to separate the dense from non-dense tissue and remove the off breast area region from the analysis. PD was calculated as the total dense area normalized by the total breast area to give the percentage of dense breast tissue as the measure of PD.

Automated Percentage of Breast Density

The wavelet expansion is the basis for the $PD_a$ application, lowering the spatial resolution, and applying the SDN analysis. The wavelet expansion of a given image is given by:

$$r_{0i} = d_1 + d_2 + d_3 + d_j + \ldots d_J + f_J \qquad \text{Eq. (1)}$$

In this expression, the subscript, i, on $r_0$ is used to define the three data representations: raw image (i=r), transformed-raw image (i=t), or the clinical display processed image (i=p). The $d_j$ images are band-pass filtered versions of $r_{0i}$ (expansion components). The $d_j$ representation is an octave sectioning of the Fourier frequency plane, where $f_j$ is a coarse version of $r_{0i}$, depending on the termination value for j. This decomposition may be described as a fine-coarse component representation of $r_{0i}$. When the raw image dimension is $n_x \times n_y$ pixels (in the x and y direction) the expansion image has the same dimension.

When operating on the full resolution data for the $PD_a$ processing, let J=1 in Eq. (1) giving $$r_{0i} = d_1 + f_1. \qquad \text{Eq. (2)}$$

Specifically, the $d_1$ and $f_1$ images are complementary high and low half-band filtered versions of $r_{0i}$. In the next step, a global-reference variance signal is estimated by using all the pixels in the $d_1$ image (corresponding to the breast region). A relatively small n×n pixel search window is maneuvered across the $d_1$ image constrained to the breast area with n=4 (rule of thumb). At each window location, the local variance is calculated. The window is moved in box-width shifts blanketing the breast region, giving the local variance image. This local variance image can be manipulated as a reduced spatial-resolution image with $n_x/n \times n_y/n$ pixels in each dimension. At each window location, the global reference is compared with the local variance. When the local variance deviates too far above the reference using a chi-square test, the respective n×n region is labeled as fibroglandular (i.e. dense). This process results in a binary image with each pixel labeled as either dense or other. The global reference variance is then refined by restricting its second (repeated) estimation in the $d_1$ image to those locations that were initially labeled as other in the first search procedure. The search window process (described above) is repeated with the refined global reference variance resulting in the binary labeled output image analogous to that provided by PD. In the final detection process, the other labeled pixels correspond to adipose image regions in $r_{0i}$. The percentage of breast density is calculated in the same manner as PD (a ratio). Each search (detection) stage requires it own significance value of 0.1 and 0.0001, respectively, for these datasets. Changing these will modify the detection thresholds. These parameters may be modified when the data representation changes, as they affect the detection thresholds and automated density labeling.

The detection process may be accessed to determine if it was affected by the image resolution. Eq. (1) may be used to lower the raw image spatial resolution before applying the $PD_a$ processing With some rearranging, the image at lower resolution may be expressed as:

$$f_1 = r_{0i} - d_1. \qquad \text{Eq. (3)}$$

Because $f_1$ is a low-pass filtered (half-band) version of $r_{0i}$, it can be down sampled (or collapsed) by discarding every other pixel row-wise and then column-wise creating an image with a 140 micron pixel resolution (half the spatial size in each dimension indicating the pixel spacing has doubled). The same analysis may be performed on the lower resolution image as that of the full resolution raw image (i.e. $f_1$ takes the place of $r_{0i}$ in Eq. (1)).

The PDa algorithm is based on certain approximations and stochastic relationships. These details are discussed because they connect the algorithm's operation to breast tissue, breast density, and the imaging process. The signal dependent noise (SDN) analysis is based on an approximation of the validity of switching time (i.e. serial) averages (mean and variance for example) with spatial averages of limited spatial extent as described previously (30). A serial average in this context implies imaging the same object (patient) repeatedly and estimating distribution quantities from a fixed pixel location (or any fixed location). Because a given image is only acquired once and mammograms have long-range positive correlation, an assumption may be made that summary measures from a small n×n region about a fixed location in one image approximates the distribution of taking n2 serial acquisitions and examining the respective summary measures from a fixed location in the vicinity of the n×n region in the same image. These arguments with the underlying Poisson process connect the PDa measure with underlying imaging physics.

Preprocessing

As an initial evaluation step, 10 case observations were selected randomly from the dataset with their 20 matched controls and processed with $PD_a$. The $PD_a$ operation did not label properly when applied to the raw images, as assessed visually. The raw images are intensity reversed relative to film-mammograms (regions of decreased mammographic density are related to large pixel values and vice versa). Reversing this relationship with a linear transformation did not alter the performance. For these reasons, the raw images may be preprocessed using an empirical based mapping given by:

$$r_{0t} = \frac{a_0}{[(m_0 \times r_{0r}) + 1]^k}, \qquad \text{Eq. (4)}$$

where $a_0$ and k are parameters determined with the optimization procedure. In this equation, the pixel values of $r_{0r}$ were linearly mapped between (0, 1). The $m_0$ factor is an empirically determined scaling constant ≈101, which constrains the pixel values to the allowable dynamic range, and was derived by generalizing the normalization method used for calibration. The m0 factor is the average current×time (mAs) system readout from a random sample of mammograms. The form of the denominator (addition of one), prevents pixel values in $r_{0t}$ from reaching infinity. Equation (4) defines the raw-transformed image representation and is similar to a gamma correction but with a negative power-law (i.e. it is normally positive for the gamma correction). This thirty image dataset described above may be used to find these two unknown parameters using an evolutionary optimization strategy.

Differential evolution (DE) optimization was used to determine the two free-parameters in Eq. (4). DE is an evolutionary process that creates a higher-ordering of the possible solution space via competition. In this scheme, the 30 random samples (i.e. $r_r$) were processed with $PD_a$. The corresponding PD quantities determined from Cumulus as the reference may be used, or target value, and minimized the $L_1$ difference, $|PD_a(r_{0t}) - PD|$, between the respective $PD_a$ and PD image pairs by summing over these differences in the 30 image dataset (i.e. the error or fitness function). For reference, the same definitions for the DE parameters may be used as its founders: the vector field population is NP=10 random vectors, which is a rule of thumb for the population size for two unknown parameters, the crossover was CR=0.1, and the evolutionary amplification factor was F=0.5. The number of generations was fixed with G=100. In brief, DE incrementally finds the parameters by minimizing the error function (fitness) by repeated processing of the 30 image pair dataset with parameter vector competitions. This process was initialized with 10 (i.e. NP) two-component random vectors with components corresponding to $A_0$ and k. $A_0$ was constrained to this range [1000, 25000] and k to this range [1,10]. A uniform random distribution defined over this range (0, 1) was used for the vector field initialization (i.e. 10 two-component parameter vectors with random values for the generation-zero population). The Cumulus method output was matched above as the primary experiment because it minimized the amount of training data used in this report, limiting the possibility of over fitting. The parameters of Eq. (4) were determined with the optimization methods described above and used those parameters for the analysis after implementing the optimization process once and evaluated the associations with breast cancer. To further evaluate the variability in the approach while limiting over fitting, the optimization was fitted for 10 additional trials (30 samples in each trial). The variability in the parameters was estimated and evaluated its impact on the logistic regression analysis relative to the findings from the first realization. To induce variability, 10 cases were selected at random and selected the respective 20 controls without replacement. The solution to Eq. (4) was found by defining one additional trial. In the next trial these 10 cases and 20 controls were removed from the random selection process and so on. To assess the (k, A0) parameter set variability impact on the breast cancer associations, three additional raw-transformed representations were created using the parameter set determined by the minimum and maximum values of k and the respective a0 (that was determined with each k) and the set formed by the distribution averages of k and a0 distributions. The raw data was transformed with each parameter set and processed them with PDa.

Signal Dependent Noise Analysis

The $PD_a$ performance is related to how pronounced the local variation presents in the $d_1$ image relative to areas of increased density in $r_{0i}$. This relationship may be captured by considering the signal dependent noise (SDN) characteristic of a given mammogram. This SDN analysis is not used in the $PD_a$ process, but is applied for algorithmic-diagnostic purposes to understand the $PD_a$ processing. Briefly, this approach also uses the $d_1$ wavelet image to estimate the local noise variance and the $f_1$ image to estimate the respective local signal average. This method may be applied to the three $r_{0i}$ representations and made comparisons. The SDN functional relationship may be modified and the data fit to this more empirically driven general model $$y = c_0 + c_1 x + c_2 x^2 + c_3 x^3 + c_4 \exp(-z)^2, \quad \text{Eq. (5)}$$

where y is the local noise variance, x is corresponding local signal, $$z = \frac{x - c_5}{c_6},$$

and the $c_i$ are the fit coefficients. This expression is general and was tailored to each representation by observation. For the raw data (i=r), $c_3 = c_4 = c_5 = c_6 = 0$, for the transformed raw data (i=t); $c_4 = c_5 = c_6 = 0$, and for the processed data (i=p); and $c_3 = 0$. Both the signal and noise values were mapped between (0, 1) before applying the curve-fitting analysis. Representative examples are provided to show the differences. Each representation's fit-coefficient distributions may be summarized with the mean and 95% confidence intervals. Equation (5) is used to provide an approximate description of SDN relationships and was fitted with non-linear regression techniques automatically after designating the form of Eq. (5) for a given representation. In this disclosure, $c_0$ is a bias term used as degree of freedom, or flexibility, in the fitting processes, and is not discussed in detail. In this SDN analysis, all case and control images (CC views only) may be used, excluding small image areas with calcifications in the applicable images. The presence of calcifications can skew the SDN relationship because they may appear as discontinuous abrupt localized spatial changes in the $d_1$ image. Calcification areas were marked manually, annotated in the automatically segmented mask images (qualified below), and then excluded from the automated analysis. This analysis was constrained to the interior breast area region corresponding to where the breast was in contact with the compression paddle. This region may be estimated by eroding the breast area along a radial direction by 25% using an automated method creating the mask defined above. It is noted that the manual exclusion of calcified areas was only used for the SDN modeling and not for the automated PDa processing used in the case-control evaluation, where the presence of calcifications is irrelevant for its operation.

To show differences in the raw-transformed data due to the spatial resolution change, the SDN fitted polynomial positive concavity may be measured for the third degree polynomial (truncated) embedded in Eq. (5). Making the assumption x (local signal average) is continuous, the graph of y (corresponding local variance) has positive concavity at $[x_1, y(x_1)]$, where $x = x_1$ when $y''(x_1) > 0$. Because x is never negative, there are one of two conditions that exist to have positive concavity at x given by $$x > \frac{-c_2}{2c_3} \text{ for } c_3 > 0 \text{ and} \quad \text{Eq. (6)}$$

$$x < \frac{-c_2}{2c_3} \text{ for } c_3 < 0.$$

For a given curve (patient) only one condition applies. The positive concavity degree may be assessed for each patient at y(x) for each value of x for both resolutions and made comparisons. The proportion of y(x) may be provided with positive concavity for all observations. The justification for this analysis and restriction to the raw-transformed data will become clear when presenting the graphs.

The above may be implemented on a computing device.

Results

The patient characteristics are summarized overall and by case-control status (see, Table 1).

TABLE 1

| variable | Case (n) | mean | SD | Control (n) | mean | SD | Total (n) | mean | std | P |
|---|---|---|---|---|---|---|---|---|---|---|
| Age (yrs.) | 192 | 64.2 | 10.6 | 358 | 64.3 | 10.6 | 550 | 64.3 | 10.7 | — |
| BMI (kg/m$^2$) | 188 | 29.0 | 6.4 | 335 | 28.8 | 6.2 | 523 | 28.9 | 6.3 | 0.81 |
| PD$_a$ (trans) | 192 | 21.0 | 7.3 | 358 | 19.1 | 7.3 | 550 | 19.8 | 7.4 | 0.002 |
| PD$_a$ (proc) | 192 | 19.1 | 7.9 | 358 | 16.9 | 7.5 | 550 | 17.6 | 7.7 | 0.0005 |
| PD (raw) | 192 | 15.0 | 12.1 | 358 | 13.6 | 12.5 | 550 | 14.1 | 12.4 | 0.17 |
| PD (proc) | 192 | 18.1 | 10.3 | 358 | 16.9 | 10.0 | 550 | 17.4 | 10.1 | 0.15 |

Table 1 shows patient characteristics and lists the distribution of relevant patient characteristics (variable) and breast density measures for the cases, controls, and overall. The breast density measures include: (1) the automated percentage of breast density measure (PD$_a$) applied to the raw-transformed images (trans); (2) PD$_a$ applied to the clinical display processed images (proc); (3) operator assisted percentage of breast density measure (PD) applied to the raw images (raw); and (4) PD applied to the clinical display processed images. The mean and standard deviation (SD) are provided for each characteristic. The respective case-control quantities were compared using conditional logistic regression (Wald test).

Some patients (cases and controls) were excluded from the study due to the presence of implants, bilateral cancer, or corrupt images (i.e. breast areas that were larger than that of the detector FOV) and their respective images were not processed with PD or PD$_a$. Thus, the final patient dataset used in the PD and automated PD$_a$ processing and subsequent analysis was comprised of 192 cases and 358 controls giving a 1:2 case and control matching ratio for 166 cases and 1:1 ratio for 26 cases. Age and BMI were similar across the cases and controls. PD$_a$ quantities from the raw data could not be calculated using this algorithm without pre-processing, as discussed below. Mean PD$_a$ for cases from both the raw-transformed and clinical display representation images was larger than for controls. The respective means from PD follow the same trend, although the differences were not statistically significant. Although the respective inter-SD quantities vary, the SD findings across the case-control sets for a given measurement are similar.

PD assessed on the raw images was a significant risk factor for breast cancer (see, Table 2), shown below. This was seen when examining associations of breast cancer in the adjusted PD [OR for quartiles: 1.00 (ref.); 1.59 (0.93, 2.70); 1.70 (0.95, 3.04); 2.04 (1.13, 3.67); and Az=0.57 (0.52, 0.62)], or continuous PD [OR per SD: 1.21 (0.97, 1.51); and Az=0.57 (0.51, 0.62)]. PD from the clinical display images was also a risk factor in both the adjusted quartile [OR: 1.00 (ref.): 1.31 (0.79, 2.18); 1.14 (0.65, 1.98); 1.95 (1.09, 3.47); and Az=0.57 (0.53, 0.62)] and continuous [OR: 1.22 (0.98, 1.51); and Az=0.55 (0.50, 0.60)] models. The ROC curves for the continuous (unadjusted) PD models are shown in FIG. 1, which shows breast density measurement receiver operating curve analysis. FIG. 1 shows sensitivity and 1-specificity for unadjusted continuous density measures with breast cancer. For the raw-transformed PDa Az=0.606 (top-left), raw PD Az=0.567 (top-right), processed PDa Az=0.603 (bottom-left), and processed PD Az=0.551 (bottom-right). The ROC curves are bolder than the no-discrimination line.

TABLE 2

| PD$_a$ Raw Transformed | Control N | Case N | unadjusted | adjusted with BMI | PD Raw | Control N | Case N | unadjusted | adjusted with BMI |
|---|---|---|---|---|---|---|---|---|---|
| Quartile 1 [3.98, 13.41) | 89 | 30 | 1.00 | 1.00 | Quartile 1 [0.00, 4.81) | 89 | 35 | 1.00 | 1.00 |
| Quartile 2 [13.41, 18.14) | 90 | 40 | 1.26 (0.73, 2.18) | 1.27 (0.74, 2.19) | Quartile 2 [4.81, 10.09) | 90 | 50 | 1.48 (0.88, 2.49) | 1.59 (0.93, 2.70) |
| Quartile 3 [18.14, 23.82) | 89 | 50 | 1.85 (1.05, 3.26) | 1.86 (1.05, 3.28) | Quartile 3 [10.09, 18.69) | 89 | 49 | 1.46 (0.85, 2.51) | 1.70 (0.95, 3.04) |
| Quartile 4 [23.82, 38.47] | 90 | 72 | 2.93 (1.64, 5.22) | 3.00 (1.67, 5.38) | Quartile 4 [18.69, 76.84] | 90 | 58 | 1.70 (1.00, 2.87) | 2.04 (1.13, 3.67) |
| AZ | | | 0.605 (0.569, 0.643) | 0.606 (0.549, 0.654) | AZ | | | 0.553 (0.520, 0.599) | 0.575 (0.523, 0.624) |
| Per 1 SD increase | | | 1.39 (1.13, 1.70) | 1.40 (1.14, 1.71) | Per 1 SD increase | | | 1.14 (0.94, 1.39) | 1.21 (0.97, 1.51) |
| AZ | | | 0.606 (0.559, 0.648) | 0.597 (0.550, 0.647) | AZ | | | 0.567 (0.508, 0.624) | 0.566 (0.507, 0.619) |
| PD$_a$ Processed | Control N | Case N | unadjusted | adjusted with BMI | PD Processed | Control N | Case N | unadjusted | adjusted with BMI |
| Quartile 1 [2.99, 10.72) | 89 | 27 | 1.00 | 1.00 | Quartile 1 [1.11, 9.63) | 89 | 39 | 1.00 | 1.00 |
| Quartile 2 [10.72, 15.80) | 90 | 50 | 1.80 (1.04, 3.12) | 1.79 (1.04, 3.11) | Quartile 2 [9.63, 15.07) | 90 | 51 | 1.28 (0.77, 2.13) | 1.31 (0.79, 2.18) |
| Quartile 3 [15.80, 22.14) | 89 | 44 | 1.61 (0.90, 2.88) | 1.61 (0.90, 2.88) | Quartile 3 [15.07, 21.39) | 89 | 40 | 1.04 (0.61, 1.76) | 1.14 (0.65, 1.98) |

TABLE 2-continued

| Quartile 4 [22.14, 35.37] AZ | 90 | 71 | 2.89 (1.64, 5.09) 0.602 (0.553, 0.647) | 2.94 (1.66, 5.19) 0.610 (0.565, 0.655) | Quartile 4 [21.39, 67.10] AZ | 90 | 62 | 1.68 (1.00, 2.83) 0.563 (0.523, 0.601) | 1.95 (1.09, 3.47) 0.573 (0.526, 0.622) |
| Per 1 SD increase AZ | | | 1.42 (1.16, 1.72) 0.603 (0.560, 0.652) | 1.43 (1.17, 1.74) 0.600 (0.548, 0.649) | Per 1 SD increase AZ | | | 1.15 (0.95, 1.38) 0.551 (0.502, 0.599) | 1.22 (0.98, 1.51) 0.551 (0.500, 0.603) |

Table 2 illustrates a percentage of breast density associations with breast cancer. This table provides the breast cancer quartile and continuous breast density associations with breast cancer for (1) the automated measure ($PD_a$) applied to the raw-transformed (top-left) and processed clinical display (bottom-left) representation images; and (2) the operator-assisted measure (PD) applied to the raw (top-right) and processed clinical display (bottom-right) representations images. Odds ratios (ORs) are cited with 95% confidence intervals (CIs) parenthetically and the area under the receiver operating characteristic curve (Az) is provided for each model with 95% CIs. CIs are cited below the respective quantities, parenthetically. Az was calculated within matched case-control pairs to utilize the design. SD is calculated from the control distribution. The quartile cutoff for each measure is also provided in the left hand column of each sub-table.

Figure 2:
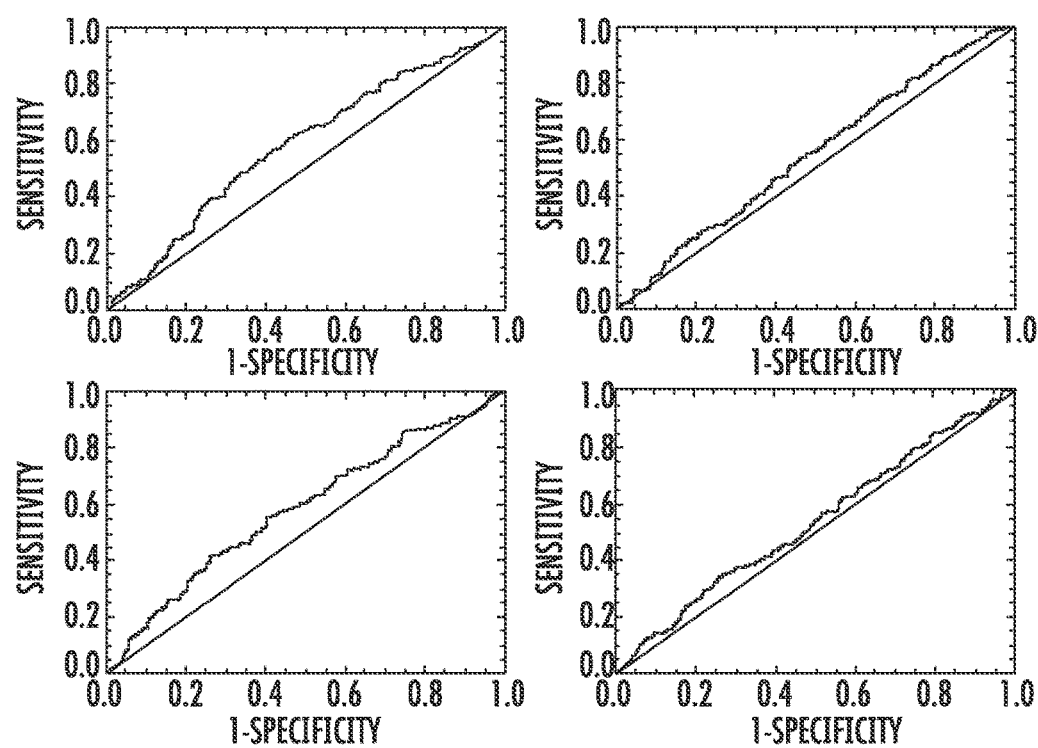
FIG. 2 illustrates an example mammogram representation.

For the $PD_a$ measure, the raw images were pre-processed prior to estimation. The DE optimization process gave k≈2.12 and $a_0$≈24813. The raw images were then processed with Eq. (4) to produce the $r_{0t}$ images, which then take the position of the raw images. FIG. 2 shows an example mammogram in the three representations: the raw image, $r_{0r}$, (left); raw-transformed image, $r_{0t}$, (middle); and the processed clinical display, $r_{0p}$, (right). The outline in $r_{0r}$ in FIG. 2 defines a region of interest (ROI) used for illustration purposes below.

Figure 3:
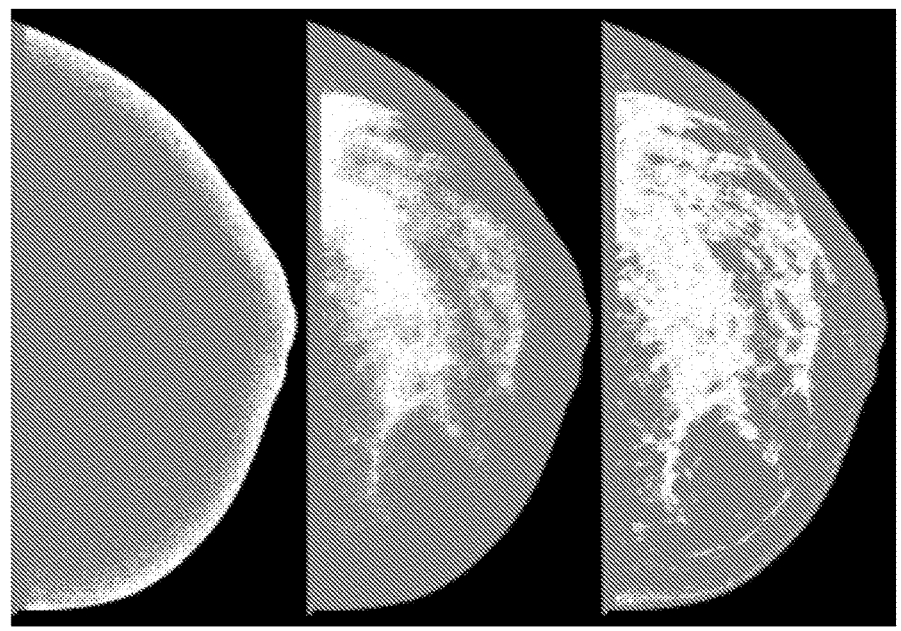
FIG. 3 illustrates an example automated percentage of breast density labeling.
Figure 4:
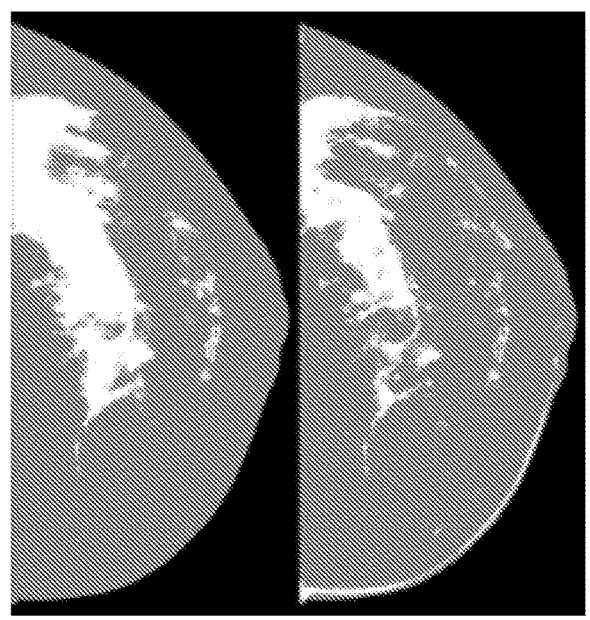
FIG. 4 illustrates examples of operator-assisted percentage of breast density measure labeling.

Examples of the breast density processing for $PD_a$ are shown in FIG. 3 and PD in FIG. 4. FIG. 3 is representative of the $PD_a$ output for the raw data without pre-processing indicating that percentage of breast density estimates were not accurate or comparable to those provided by PD, and therefore, not estimated. From left to right, FIG. 3 shows the raw (left), the raw-transformed (middle), and clinical display images (right). The respective breast density measurements were: (i) not estimated; (ii) 25.5%; (iii) and 33.4% FIG. 4 shows the operator-assisted breast density measure (PD) results for the raw (left) and clinical display (right) images shown in FIG. 2. The respective breast density measurements were: (i) 19.8%; (ii) and 13.8%.

$PD_a$ on the raw-transformed images was significantly associated with breast cancer (Table 2) in the adjusted [OR for $PD_a$ quartiles: 1.00 (ref.); 1.27 (0.74, 2.19); 1.86 (1.05, 3.28); 3.00 (1.67, 5.38); and Az=0.61 (0.55, 0.65)] and continuous [OR: 1.40 (1.14, 1.71) per SD; and Az=0.60 (0.55,0.65)] models. $PD_a$ on the clinical display images also resulted in significant risk factor (Table 2) and Az estimates in both the adjusted quartile [OR; 1.00 (ref.); 1.79 (1.04, 3.11); 1.61 (0.90, 2.88); 2.94 (1.66, 5.19); and Az=0.61 (0.56, 0.65)] and continuous [OR: 1.43 (1.17, 1.74); and Az=0.60 (0.55, 0.65)] models. The ROC curves for the continuous $PD_a$ models (unadjusted) are also shown in FIG. 1. Comparing the inter-measure Az for the continuous models for the $PD_a$-raw-transformed/PD-raw images gave p=0.18 (0.606 vs. 0.567) and p=0.04 (0.603 vs. 0.551) for the $PD_a$-processed/PD-processed images indicating $PD_a$ provided marginally greater predictive capability than PD for the processed representation data. The $PD_a$ processing takes approximately 15 seconds per small FOV image and 27 seconds per large FOV image with our server (average times taken over the dataset).

To assess variability in our raw-transform representation findings, the optimization process described in the "Preprocessing" section above may be run multiple times without including the results from above. This gave (2.59, 22395) for the mean, (1.92, 20105) for the minimum, and (3.52, 23439) for the maximum (k, $A_0$) parameter sets. The $PD_a$ findings from processing the raw images with these additional sets are provided in Table 3 below. The ORs and Az findings are similar to those shown in Table 2 for the raw-transformed images. Although the endpoint associations with breast cancer are similar, the quartile cutoffs vary inducing variation in the number of cases in each quartile.

TABLE 3

| $PD_a$ Raw-transformed (Min) | Control N | Case N | un-adjusted | adjusted with BMI | $PD_a$ Raw-transformed (Mean) | Control N | Case N | un-adjusted | adjusted with BMI | $PD_a$ Raw-transformed (Max) | Control N | Case N | un-adjusted | adjusted with BMI |
| --- | --- | --- | --- | --- | --- | --- | --- | --- | --- | --- | --- | --- | --- | --- |
| Quartile 1 [1.56, 7.25) | 89 | 32 | 1.00 | 1.00 | Quartile 1 [2.62, 10.91) | 89 | 35 | 1.00 | 1.00 | Quartile 1 [4.06, 15.10) | 89 | 35 | 1.00 | 1.00 |
| Quartile 2 [7.25, 10.94) | 90 | 45 | 1.42 (0.82, 2.46) | 1.44 (0.83, 2.49) | Quartile 2 [10.91, 15.61) | 90 | 40 | 1.13 (0.65, 1.98) | 1.14 (0.65, 2.00) | Quartile 2 [15.10, 20.85) | 90 | 43 | 1.19 (0.69, 2.06) | 1.20 (0.69, 2.07) |
| Quartile 3 [10.94, 16.08) | 89 | 47 | 1.52 (0.88, 2.64) | 1.53 (0.88, 2.67) | Quartile 3 [15.61, 20.79) | 89 | 43 | 1.29 (0.75, 2.24) | 1.31 (0.76, 2.28) | Quartile 3 [20.85, 25.02) | 89 | 47 | 1.36 (0.79, 2.34) | 1.38 (0.80, 2.38) |
| Quartile 4 [16.08, 31.94] AZ | 90 | 68 | 2.45 (1.39, 4.32) 0.58 (0.54, 0.63) | 2.55 (1.44, 4.54) 0.60 (0.55, 0.64) | Quartile 4 [20.79, 34.42] AZ | 90 | 74 | 2.35 (1.36, 4.06) 0.59 (0.54, 0.63) | 2.45 (1.41, 4.27) 0.60 (0.55, 0.65) | Quartile 4 [25.02, 34.98] AZ | 90 | 67 | 2.05 (1.19, 3.54) 0.59 (0.53, 0.62) | 2.10 (1.21, 3.66) 0.59 (0.53, 0.63) |

TABLE 3-continued

| Per 1 SD increase | 1.40 (1.15, 1.72) | 1.44 (1.17, 1.77) | Per 1 SD increase | 1.37 (1.12, 1.67) | 1.39 (1.13, 1.70) | Per 1 SD increase | 1.26 (1.03, 1.53) | 1.27 (1.04, 1.55) |
| AZ | 0.62 (0.57, 0.66) | 0.60 (0.56, 0.65) | AZ | 0.60 (0.55, 0.64) | 0.59 (0.55, 0.65) | AZ | 0.59 (0.53, 0.64) | 0.60 (0.54, 0.64) |

Figure 5:
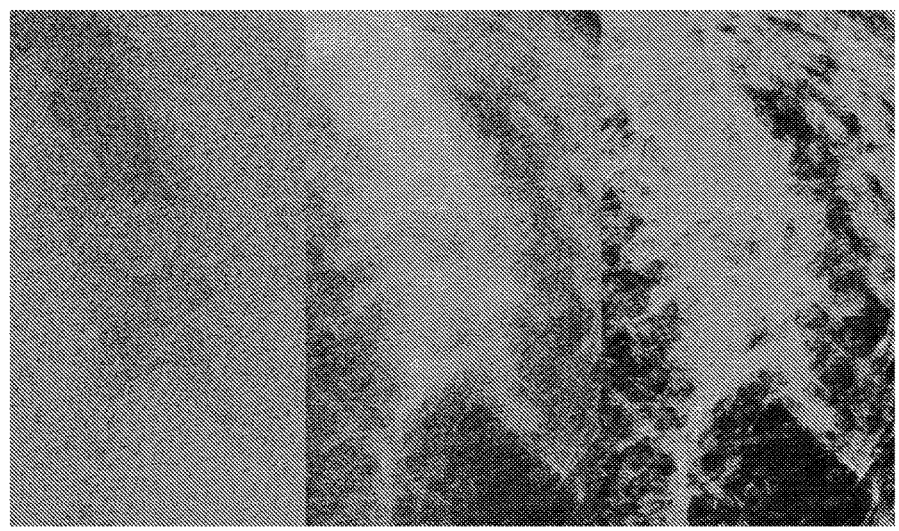
FIG. 5 illustrates a local variance region of interest.

Comparing the $PD_a$ (applied to either $r_{0t}$ or $r_{0p}$) automated labeling in FIG. 3 with the corresponding PD results in FIG. 4 shows the two methods operate differently. As noted within the broad dense regions, $PD_a$ detects (labels) locally, whereas PD appears to use a contoured based threshold (i.e. a more global detection). This operational difference is noted by the salt and pepper appearance in the $PD_a$ image in comparison with the respective broad uniformly dense regions in the PD image. The effect on the $PD_a$ processing due to the different representations is further exemplified in the local-variance images shown in FIG. 5, corresponding to the region of interest (ROI) marked in FIG. 2 (left image). These ROIs were equalized by adjusting the window levels and widths similarly for caparison (see captions). The local variance in the raw representation (left) shows little contrast. The raw-transformed (middle) and clinical display (left) variance representations show distinct contrast differences, most notable in glandular-adipose transition regions. Intra and inter-measurement correlation analyses for these measures are provided in Table 4. The inter-measure correlation is less than 0.50 when considering the raw/raw-transformed and processed/processed comparisons between PD and $PD_a$. As expected, the intra-measure analysis provided better agreement when considering either the raw/processed comparison for PD or the raw-transformed/processed comparison for $PD_a$. It is interesting to note, $PD_a$ provided increased inter-measure agreement (0.87 compared with 0.73 from PD).

TABLE 4

| Measurement | PD raw | PD proc | $PD_a$ raw-trans | $PD_a$ proc |
| --- | --- | --- | --- | --- |
| PD raw | 1.00 | 0.73 | 0.37 | 0.46 |
| PD proc | 0.73 | 1.00 | 0.38 | 0.43 |
| $PD_a$ raw-trans | 0.37 | 0.38 | 1.00 | 0.87 |
| $PD_a$ proc | 0.46 | 0.43 | 0.87 | 1.00 |

Table 4 illustrates correlation coefficients and lists the inter and intra measure Pearson correlation coefficients for PD and $PD_a$. PD was applied to the raw and clinical display processed (proc) images, whereas $PD_a$ was applied to the raw-transformed (raw-trans) and processed (proc) images.

Figure 6:
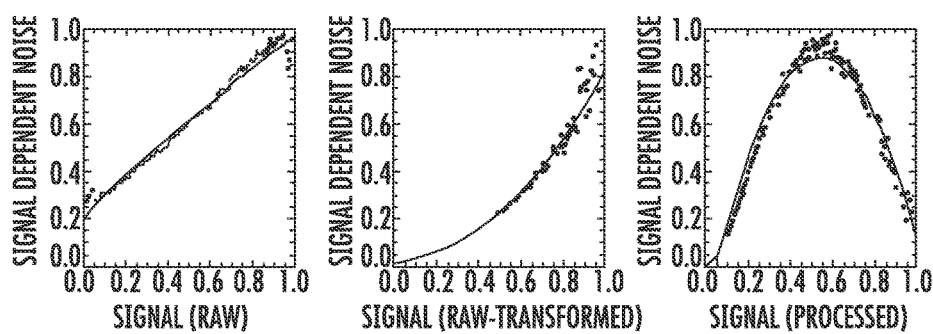
FIG. 6 illustrates an example signal dependent noise analysis.

The differences, noted above, are further qualified by the corresponding SDN modeling analysis and representative plots shown in FIG. 6. The raw data (left) shows a slight deviation from a linear model, whereas the raw-transformed data (middle) requires a third degree polynomial to capture the trend, and the processed data (right) exhibits a non-monotonic non-linear trend. In FIG. 6, From left to right, the fitted coefficients are: (c0, c1, c2)≈(0.209, 0.885, −0.133), (c0, c1, c2, c3)≈(0.016, 0.094, 0.607, 0.483), and (c0, c1, c2, c5, c6)≈(−0.195, 3.92, −3.59, −0.050, 0.999, 0.002).

Summary results (entire dataset) for the SDN models corresponding to each data representation are provided in Table 4. Both the raw and raw-transformed representations share a monotonic quality but differ in character. The linear trend of the raw data can be gauged by comparing the magnitudes of its $c_1$ (linear) and $c_2$ (quadratic) coefficient summaries (see, Table 5), whereas the raw-transformed data exhibits a stronger non-linear or quadratic tendency as noted by comparing its $c_2$ (quadratic), $c_1$ (linear) and $c_3$ (cubic) coefficients. The monotonic and non-linear form of the raw-transformed data is also a distinguishing characteristic. In contrast with the raw and raw-transformed representations, the clinical display representation data (right) exhibits non-linear but non-monotonic behavior as gauged by the relative magnitude of its $c_4$ coefficient in comparison with its linear and quadratic coefficients (i.e., $c_1$ and $c_2$). The non-linear and monotonic increase of the raw-transformed data relationship is distinguishing characteristics of its SDN characteristic. These findings suggest the nonlinear attributes are beneficial for the $PD_a$ processing because they induce contrast in the variance representation images (see FIG. 5), which gives the foundation for estimating the reference variance for a given mammogram with improved precision.

TABLE 5

| | Image representation | | |
| Coefficients | raw | raw-trans | proc |
| --- | --- | --- | --- |
| $c_0$ | 0.140 (0.130, 0.150) | 0.019 (0.017, 0.021) | −0.111 (−0.116, −0.106) |
| $c_1$ | 0.455 (0.410, 0.501) | 0.274 (0.255, 0.293) | 3.001 (2.926, 3.076) |
| $c_2$ | 0.131 (0.098, 0.164) | 0.339 (0.265, 0.414) | −2.265 (−2.390, −2.141) |
| $c_3$ | — | 0.106 (0.047, 0.165) | — |
| $c_4$ | — | — | −0.433 (−0.538, −0.328) |
| $c_5$ | — | — | 1.038 (1.016, 1.060) |
| $c_6$ | — | — | 0.083 (0.064, 0.102) |

Discussion

The above provides a validation of the $PD_a$ method for FFDM images acquired from Hologic technology. The $PD_a$ findings from both the raw-transformed and processed images are similar to PD in breast cancer association with comparable ORs and greater Az. The raw-transformed images and findings are used in place of the raw mammograms. The results in this report confirm our earlier findings from digitized film (29). However, the OR associations for this report provided by both PD and $PD_a$ appear to be somewhat attenuated relative to other studies of digitized film, whereas the Az relationships are in agreement with reported values. This could be a function of the relatively small sample size or density assessed from digital mammograms.

The associations provided by $PD_a$ from the raw data required a transformation. The form of this transformation was based on heuristic considerations and may not be optimal, although this transform produced a validated percentage of breast density measure in this report. The work involved training with a relatively small subset of images (30 from 550 images) and the $PD_a$ algorithm is relatively straight forward. Therefore, the method will perform equally as well under similar circumstances with other datasets (i.e. from the same FFDM technology). There are two adjustable detection parameters, in addition to those parameters defined in Eq. (4) that will require modification when addressing other data representations (e.g. different detector technologies). There are also various methods that could be used to train the $PD_a$ algorithm each with its own limitations. Ideally, breast cancer status could be used as the endpoint when developing a measure for risk applications because it is the known without ambiguity, eliminating the requirement for matching to another density measure. Breast cancer status was not used as the endpoint for training because it would have required the entire dataset for training (i.e. increase the possibility of over fitting). Also, it would lead to protracted training times.

The above also does not consider either intra or inter operator variability influences. Considering operator influence may be important when designing a measure such as the BI-RADS breast composition descriptor, as this metric was designed to capture the radiologist's overall impression. The association with breast cancer and the overall radiologist's impression endpoints may not be equivalent (44), but are equally important. The (k, $a_0$) variability analysis shows there is latitude in the data representation indicating that the breast density assignments at the patient level can vary considerably across the dataset while keeping consistent associations with breast cancer. This may be attributable to a number of factors including an isolated reader, the ambiguous nature of breast density, or both. The correlation analysis between PD and our measures was somewhat less that shown previously with digitized-film data (29). These differences may be due to the way the two methods detect breast density, differences in the data representation (i.e. film compared to this form of FFDM), or to the limited number of training samples used in the report. The above may be trained with the breast cancer endpoint status using the dataset herein, and then a validation of $PD_a$ performed with an independent dataset of similar proportion that is under construction to develop a measure for risk applications. A PD-type measure has been developed (herein "$PD_c$") using calibrated images from other FFDM technologies which could be used to train the $PD_a$ algorithm to reduce variation. We also used both clinical display and raw data in the analysis.

Additionally, the above provides an analysis based on SDN to explain the $PD_a$ performance. When the Poisson process approximation holds, a linear relationship is shown between the noise and signal as approximated with the raw data (FIG. 6 on the left). The findings suggest that a near-linear relationship does not offer sufficient contrast between the glandular variation and that of the adipose variation (FIG. 5 on the left) for the $PD_a$ process to operate effectively. These findings indicate that the non-monotonic characteristic of the clinical display images offers sufficient contrast but dense tissue may be lost on the right side of the crest because the variation from the adipose and glandular noise signals are mirrored across the crest midline. This non-monotonic behavior may be the cause for the inversion (or flat) of the respective second and third quartile ORs (Table 2) derived from $PD_a$ using the clinical display images. It is interesting to note that similar OR inversion findings resulted from PD for the clinical display images, as well. Although there are marginal differences in the $PD_a$ from the raw-transformed and processed images, the raw-transformed representation may be preferable because the quartile ORs monotonically increase as expected (Table 2) and the Az is larger. This SDN modeling provided a coarse description that helps to understand a rather complicated process.

Although there are many automated methods under development for breast density as discussed previously, there are few studies showing that these measures show associations with breast cancer at least equivalent to that of PD. Standardized and calibrated approaches have given mixed results in producing a measure that provides equivalent or stronger breast cancer associations than given by PD. There are commercial products available that use standardized data for estimating breast density from raw FFDM images including studies that show their comparison with the clinical BI-RADS density measure and other risk factors. But, to date, there are no published data that demonstrates their association with breast cancer.

CONCLUSION

As demonstrated above, the most cost-effective frequency of mammography is dependent upon a woman's breast density, age, family history of breast cancer, and history of prior biopsies and that significant benefits, including both costs and quality of life, can be derived from personalized breast screening. There is a feasibility of acting on risk when incorporating visually assessed breast density in the screening environment, underscoring the need for an reproducible automated measure.

The above presents and validates an automated approach for estimating the percentage of breast density for FFDM applications. A diagnostic process for assessing the automated measurement's ability to operate properly when presented with a foreign data representation was also presented. The diagnostic procedure is complementary to the automated measure and helps to ensure its generalization to other types of datasets. Automated breast density measurements are likely required for industrial-scale clinical applications, as not to hinder clinical-throughput and to maintain measurement consistency. The $PD_a$ is a valid candidate for further evaluation for possible inclusion in clinical environment. The present disclosure is timely because over 82% of the accredited mammography facilities in the US operate FFDM units, and this particular FFDM technology accounts for about 70% of the market share in the U.S. The present disclosure shows that either the raw (after transforming) or clinical display images can be processed with $PD_a$ from this technology with minor loss.

What is claimed is:

1. A method of assessing breast density for breast cancer risk applications, comprising:
    receiving digital image data including a plurality of pixels;
    performing a statistical analysis on the digital image data to automate a determination of breast density ($PD_a$) by:
    applying a wavelet expansion to the digital image data to produce a multiresolutional representation comprising difference images (di images) and a low-resolution image;
    applying a signal dependent noise (SDN) analysis to at least one image of the multiresolutional representation to produce filtered image data;
    estimating a global reference variance signal from all pixels of a $d_1$ image that corresponds to a breast region of the filtered digital image data;
    moving a n×n pixel search window across the $d_1$ image, and for each n×n pixel search window location:

determining a local variance; and determining if the local variance for each n×n pixel search window location deviates from the global reference using a chi-square test, and if so, labeling a respective n×n pixel search window location with a first designation, otherwise labeling the respective n×n pixel search window location with a second designation;

producing a binary image with each pixel labeled with the first designation or the second designation;

refining the global reference variance by moving a n×n pixel search window across locations of the $d_1$ image labeled with the second designation in the binary image; and determining that the locations labeled with the second designation are adipose image regions to provide a measure of risk for breast cancer.

2. The method of claim 1, performing the statistical analysis comprising:

applying a logistic regression to model and compare the association between quartile measures of bread density (PD), and breast cancer status, with a lowest quartile measured PD.

3. The method of claim 2, further comprising summarizing determining magnitudes of the associations by odds ratios (ORs) having predetermined confidence intervals (CIs).

4. The method of claim 2, further comprising adjusting breast density models for body mass index (BMI).

5. The method of claim 1, wherein $PD_a$ is calculated as a ratio.

6. The method of claim 1, further comprising preprocessing the digital image data using mapping technique.

7. The method of claim 6, wherein the mapping technique is an empirical based mapping that is determined by:

$$r_{0t} = \frac{a_0}{[(m_0 \times r_{0r}) + 1]^k},$$

wherein $a_0$ and k are parameters determined by an optimization procedure, and wherein $m_0$ is an empirically determined scaling constant $\approx 101$, which constrains pixel values to a predetermined dynamic range, and was derived by generalizing a normalization method used for calibration.

8. The method of claim 1, further comprising determining a signal dependent noise (SDN) characteristic of the digital image data.

9. The method of claim 8, wherein the SDN is determined in accordance with:

$$y = c_0 + c_1 x + c_2 x^2 + c_3 x^3 + c_4 \exp(-z)^2,$$

where y is a local noise variance, x is a corresponding local signal, $$z = \frac{x - c_5}{c_6},$$

and the $c_i$ are fit coefficients.

10. The method of claim 1, wherein the first indication represents a dense breast tissue region and where in the second indication represents a breast tissue region having other characteristics than dense.

\* \* \* \* \*

UNITED STATES PATENT AND TRADEMARK OFFICE
CERTIFICATE OF CORRECTION

PATENT NO. : 10,007,982 B2
APPLICATION NO. : 14/893603
DATED : June 26, 2018
INVENTOR(S) : John J. Heine et al.

Page 1 of 1

It is certified that error appears in the above-identified patent and that said Letters Patent is hereby corrected as shown below:

In the Specification

Column 1, Line 5 through Line 10 should read:
STATEMENT REGARDING FEDERALLY SPONSORED RESEARCH OR DEVELOPMENT
This invention was made with government support under grant numbers CA079947, CA140286, CA177150, CA128931, CA097396, and CA116201 awarded by the National Institutes of Health and grant number DAMD17-00-1-0331 awarded by the US Army Medical Research and Materiel Command (ARMY/MRMC). The Government has certain rights in the invention.

Signed and Sealed this
Thirtieth Day of April, 2019

Andrei Iancu
*Director of the United States Patent and Trademark Office*